United States Patent
Reed et al.

[11] Patent Number: 5,830,886
[45] Date of Patent: Nov. 3, 1998

[54] STEROID SULPHATASE INHIBITORS

[75] Inventors: Michael John Reed, London; Barry Victor Lloyd Potter, Bath, both of United Kingdom

[73] Assignee: Imperial College of Science, Technology and Medicine, London, United Kingdom

[21] Appl. No.: 458,352

[22] Filed: Jun. 2, 1995

Related U.S. Application Data

[62] Division of Ser. No. 196,192, filed as PCT/GB92/01587, Aug. 28, 1992, Pat. No. 5,616,574.

[30] Foreign Application Priority Data

Aug. 29, 1991 [GB] United Kingdom ............... 9118478

[51] Int. Cl.⁶ .................................................. A61K 31/165
[52] U.S. Cl. ........................ 514/178; 514/456; 514/457; 514/459; 514/460; 514/517
[58] Field of Search .................................. 514/178, 171; 552/626

[56] References Cited

FOREIGN PATENT DOCUMENTS 114 806   8/1975   Germany .
1398026   6/1975   United Kingdom .

OTHER PUBLICATIONS

Townsley et al, Research Steriods, 5, 73–78, 1973.
Schwarz et al, Pharmagie 30, 17–21, 1975.
Zeitschrift fur Chemie, Schwarz et al 14(1) 1974 pp. 15–16.

*Primary Examiner*—Rebecca Cook
*Attorney, Agent, or Firm*—Nixon & Vanderhye P.C.

[57] ABSTRACT

Steroid sulphatase inhibitors and pharmaceutical compositions containing them for use in the treatment of oestrone dependent tumors, especially breast cancer. The steroid sulphatase are sulphamate esters of formula (I):

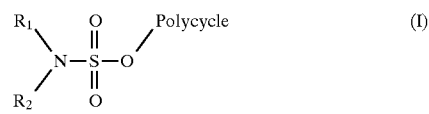

where $R_1$ and $R_2$ are each H, alkyl, alkenyl, cycloalkyl or aryl, or together represent an alkylene group optionally containing a heteroatom e.g. —O— or —NH—; and —O-polycycle represents the residue of a polycyclic alcohol such as a sterol, preferably a 3-sterol.

9 Claims, 5 Drawing Sheets

STEROID SULPHATASE INHIBITORS

This application is a division of Ser. No. 08/196,192 filed Dec. 27, 1994, now U.S. Pat. No. 5,616,574, which is a 35 U.S.C. 371 of PCT/GB92/01587 filed Aug. 28, 1992.

FIELD OF INVENTION

This invention relates to novel compounds for use as steroid sulphatase inhibitors, and pharmaceutical compositions containing them.

BACKGROUND AND PRIOR ART

Steroid precursors, or pro-hormones, having a sulphate group in the 3-position of the steroid nucleus, referred to hereinafter simply as steroid sulphates, are known to play an important part as intermediates in steroid metabolism in the human body. Oestrone sulphate and dehydroepiandrosterone (DHA) sulphate, for example, are known to play an important role as intermediates in the production, in the body, of oestrogens such as oestrone and oestradiol. Oestrone sulphate, in particular, is known, for example, to represent one of the major circulating oestrogen precursors particularly in post-menopausal women and oestrone sulphatase activity in breast tumours is 100–1000 fold greater than that of other enzymes involved in oestrogen formation (James et al., *Steroids*, 50, 269–279 (1987)).

Figure 1:
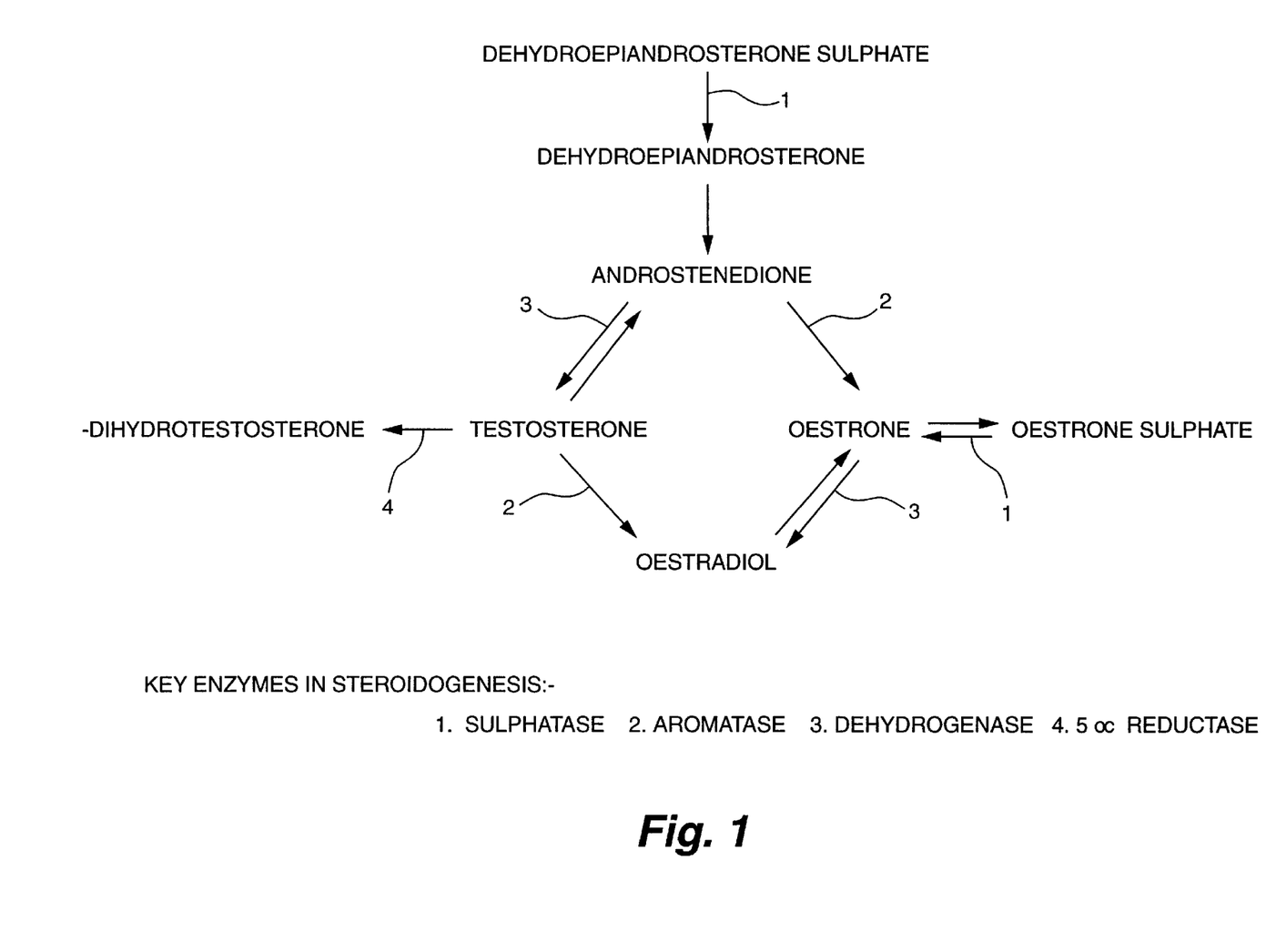
FIG. 1 is a schematic chart showing the metabolic pathways, enzymes and steroid intermediates associated with the production of oestradiol in vivo.

Not only that, but oestrogens such as oestrone and oestradiol, particularly the over-production thereof, are strongly implicated in malignant conditions, such as breast cancer, see *Breast Cancer, Treatment and Prognosis*: Ed. R. A. Stoll, pp. 156–172, Blackwell Scientific Publications (1986), and the control of oestrogen production is the specific target of many anti-cancer therapies, both chemotherapy and surgical, e.g. oöphorectomy and adrenalectomy. So far as endocrine therapy is concerned, efforts have so far tended to concentrate on aromatase inhibitors, i.e. compounds which inhibit aromatase activity, which activity is involved, as the accompanying oestrogen metabolic flow diagram (FIG. 1) shows, in the conversion of androgens such as androstenedione and testosterone to oestrone and oestradiol respectively.

In recently published International Application W091/13083 a proposal has been made to target a different point in the oestrogen metabolic pathway, or rather two different points, that is to say the conversion of DHA sulphate and oestrone sulphate to DHA and oestrone, respectively, by steroid sulphatase activity, and using 3-monoalkylthiophosphonate steroid esters as a steroid sulphatase inhibitor, more especially oestrone-3-monomethylthiophosphonate.

OBJECTS OF THE INVENTION

A first object of the present invention is to provide new compounds capable of inhibiting steroid sulphatase activity in vitro and in vivo.

A second object of the present invention is to provide new compounds having improved activity as steroid sulphatase inhibitors both in vitro and in vivo.

A third object of the invention is to provide pharmaceutical compositions effective in the treatment of oestrogen dependent tumours.

A fourth object of the invention is to provide pharmaceutical compositions effective in the treatment of breast cancer.

A fifth object of the invention is to provide a method for the treatment of oestrogen dependent tumours in mammals, especially humans.

A sixth object of the invention is to provide a method for the treatment of breast cancer in mammals and especially in women.

SUMMARY OF INVENTION

The invention is based on the discovery of novel compounds having steroid sulphatase inhibitory activity, in some cases, with extremely high activity levels. These compounds are the sulphamic acid esters of polycyclic alcohols, being polycyclic alcohols the sulphate of which is a substrate for enzymes having steroid sulphatase (EC 3.1.6.2) activity, the N-alkyl and N-aryl derivatives of those sulphamic acid esters, and their pharmaceutically acceptable salts.

Broadly speaking, the novel compounds of this invention are compounds of the Formula (I)

$$\begin{array}{c} R_1 \\ \phantom{R}\diagdown \phantom{N} \quad O \quad \phantom{S} \diagup \text{Polycycle} \\ N-S-O \\ \diagup \quad \| \\ R_2 \quad O \end{array} \qquad \text{FORMULA (I)}$$

where:

$R_1$ and $R_2$ are each independently selected from H, alkyl, cycloalkyl, elkenyl and aryl, or together represent alkylene optionally containing one or more hetero atoms or groups in the alkylene chain; and the group —O— polycycle represents the residue of a polycyclic alcohol, the sulphate of which is a substrate for enzymes having steroid sulphatase activity (EC 3.1.6.2).

As used herein the reference to polycyclic alcohols, the sulphate of which is a substrate for enzymes having steroid sulphatase activity refers to polycyclic alcohols, the sulphate of which is hydrolyzable by enzymes having steroid (E.C. 3.1.6.2) activity, viz: the derivatives of the Formula:

$$\begin{array}{c} O \quad \phantom{S} \diagup \text{Polycycle} \\ \| \\ HO-S-O \\ \| \\ O \end{array}$$

which when incubated with steroid sulphatase EC 3.1.6.2 at pH 7.4 and 37° C. and provides a Km value of less than 50 μmoles.

BRIEF DESCRIPTION OF DRAWINGS

The activity of the present compounds as steroid sulphatase inhibitors is illustrated in the accompanying drawings.

DETAILED DESCRIPTION

In one aspect the present invention provides, as novel compounds, the sulphamic acid esters of polycyclic alcohols, being polycyclic alcohols the sulphate of which is a substrate for enzymes having steroid sulphatase activity in accordance with the definition already provided, and their N-alkyl, N-cycloalkyl, N-alkenyl and N-aryl derivatives. These compounds are of Formula I hereinbefore given.

Preferably the polycyclic group will contain, inclusive of all substituents, a maximum of about 40 carbon atoms, more usually no more than about 30. Preferred polycycles are those containing a steroidal ring structure, that is to say a cyclopentanophenanthrene skeleton. Preferably, the sulphamyl or substituted sulphamyl group is attached to that skeleton in the 3-position, that is to say are compounds of the Formula II:

FORMULA (II)

where $R_1$ and $R_2$ are as above defined and the ring system ABCD represents a substituted or unsubstituted, saturated or unsaturated steroid nucleus, preferably oestrone or dehydroepiandrosterone.

Other suitable steroid ring systems are:
substituted oestrones, viz:

| | | | |
|---|---|---|---|
| 2-OH-oestrone | 2-methoxy-oestrone | 4-OH-oestrone | 6α-OH-oestrone |
| 7α-OH-oestrone | 16α-OH-oestrone | 16β-OH-oestrone | | oestradiols and substituted oestradiols, viz:

| | | |
|---|---|---|
| 2-OH-17β-oestradiol | 2-methoxy-17β-oestradiol | 4-OH-17β-oestradiol |
| 6α-OH-17β-oestradiol | 7α-OH-17β-oestradiol | 16α-OH-17α-oestradiol |
| 16β-OH-17α-oestradiol | 16β-OH-17β-oestradiol | 17α-oestradiol |
| 17β-oestradiol | 17α-ethinyl-17β-oestradiol | | oestriols and substituted oestriols, viz:

| | | |
|---|---|---|
| oestriol | 2-OH-oestriol | 2-methoxy-oestriol |
| 4-OH-oestriol | 6α-OH-oestriol | 7α-OH-oestriol | substituted dehydroepiandrosterones, viz:

| | |
|---|---|
| 6α-OH-dehydroepiandrosterone | 7α-OH-dehydroepiandrosterone |
| 16α-OH-dehydroepiandrosterone | 16β-OH-dehydroepiandrosterone |

In general terms the steroid ring system ABCD may contain a variety of non-interfering substituents. In particular, the ring system ABCD may contain one or more hydroxy, alkyl especially lower ($C_1$–$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$–$C_6$) alkoxy, e.g. methoxy, ethoxy, propoxy etc., alkinyl, e.g. ethinyl, or halogen, e.g. fluoro substituents.

Other suitable non-steroidal ring systems include: diethylstilboestrol, stilboestrol and other ring systems providing sulfates having Km values of less than 50 μmoles with steroid sulphatase EC 3.1.6.2.

When substituted, the N-substituted compounds of this invention may contain one or two N-alkyl, N-alkenyl, N-cycloalkyl or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—PhCH$_3$; o-, m- or p-). Where $R_1$ and $R_2$ represent cycloalkyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. —O— or —NH— to provide a 5-, 6- or) -membered heterocycle, e.g. morpholino pyrrolidono or piperidino.

Within the values alkyl, cycloalkyl, alkenyl and aryl we include substituted groups containing as substituents therein one or more groups which do not interfere with the sulphatase inhibitory activity of the compound in question. Exemplary non-interfering substituents include hydroxy, amino, halo, alkoxy, alkyl and aryl.

Most preferred are compounds of the Formula III and IV:

FORMULA (III)

-continued

FORMULA (IV)

where $R_1$ and $R_2$ are H or $C_1$–$C_5$ alkyl, i.e. oestrone-3-sulphamate and dehydroepiandrosterone-3-sulphamate and their N—($C_1$–$C_5$) alkyl derivatives, especially the dimethyl derivatives, $R_1$=$R_2$=$CH_3$.

The sulphamic acid esters of this invention are prepared by reacting the polycyclic alcohol, e.g. oestrone or dehydroepiandrosterone, with a sulfamoyl chloride $R_1R_2NSO_2Cl$, i.e. the reaction scheme

REACTION SCHEME I

Conditions for carrying out reaction scheme I are as follows:

Sodium hydride and a sulphamoyl chloride are added to a stirred solution of oestrone in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporation with toluene affords a crude residue which is further purified by flash chromatography.

Where necessary, functional groups in the polycyclic alcohol (sterol) may be protected in known manner and the protecting group or groups removed at the end of the reaction.

For pharmaceutical administration, the steroid sulphatase inhibitors of this invention can be formulated in any suitable manner utilising conventional pharmaceutical formulating techniques and pharmaceutical carriers, exipients, diluents etc. and usually for parenteral administration. Approximate effective dose rates are in the range 100 to 800 mg/day depending on the individual activities of the compounds in question and for a patient of average (70 kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

For particular applications, it is envisaged that the steroid sulphatase inhibitors of this invention may be used in combination therapies, either with another sulphatase inhibitor, or, for example, in combination with an aromatase inhibitor, such as for example, 4-hydroxyandrostenedione (4-OHA).

The invention is illustrated by the following preparative Examples and test data:

EXAMPLE 1

Preparation of oestrone-3-sulphamate

Sodium hydride (60% dispersion; 2 eq) and sulphamoyl chloride (2 eq) were added to a stirred solution of oestrone (1 eq) in anhydrous dimethyl formamide at 0° C. Subsequently, the reaction was allowed to warm to room temperature whereupon stirring was continued for a further 24 hours.

The reaction mixture was poured onto a cold saturated solution of sodium bicarbonate and the resulting aqueous phase was extracted with dichloromethane. The combined organic extracts were dried over anhydrous $MgSO_4$. Filtration followed solvent evaporation in vacuo and co-evaporation with toluene afforded a crude residue which is further purified by flash chromatography.

Analysis showed the following data:

$\delta^1H$ (270 MHz; $CD_3OD$): 0.91 (s, 3H, $C_{18}$—Me), 1.40–2.55 (series of m, 13H), 2.90–2.92 (m, 2H), 7.04 (br d, 2H, J=10.44 Hz), 7.33 (br d, 1H, J=8.42 Hz).

$\delta^{13}C$ (67.8 MHz; $CD_3OD$): 14.53 (q, $C_{18}$—ME), 22.80 (t), 27.24 (L), 27.73 (t), 30.68 (t), 33.05 (t), 37.01 (t), 39.76 (d), 45.73 (s, $C_{18}$), 51.86 (d), 120.76 (d), 123.54 (d), 127.89 (d), 139.83 (s), 150.27 (s), 223.87 (s, C=O).

m/z (%): 349 (9) (m$^+$), 270 (100), 213 (26), 185 (43), 172 (31), 159 (21), 146 (36), 91 (33), 69 (37), 57 (73), 43 (56), 29 (24).

Microanalysis:

|  | C | H | N |
|---|---|---|---|
| Expected: | 61.87% | 6.63% | 4.01% |
| Found: | 61.90% | 6.58% | 3.95% |

EXAMPLE 2

Preparation of oestrone-3-N-methylsulphamate

The procedure of Example 1 was repeated save that sulphamoyl chloride was replaced by the same quantity of N-methylsulphamoyl chloride.

Analysis showed the following data:

$\delta^1H$ (270 MHz; $CDCl_3$): 0.91 (s, 3H, $C_{18}$—Me), 1.28–1.68 (m, 6H), 1.93–2.60 (series of m, 7H), 2.90–2.95 (m, 2H), 2.94 (d, 3H, J=5.13 Hz, MeN—), 4.68–4.71 (br m, exchangeable, 1H, —NH), 7.02–7.07 (m, 2H), 7.26–7.32 (m, 1H).

m/z (%): 364 [M+H]$^+$

EXAMPLE 3
Preparation of oestrone-3-N,N-dimethylsulphamate

The procedure of Example 1 was repeated save that sulphamoyl chloride was replaced by the same quantity of N,N-dimethylsulphamoyl chloride.
Analysis showed the following data:

$\delta^1$H (27 OMHz; CDCl$_3$): 0.92 (s, 3H, C$_{18}$—Me), 1.39–1.75 (m, 5H), 1.95–2.60 (series of m, 6H), 2.82 (s, 3H MeN—), 2.96–3.00 (m, 4H), 2.98 (s, 3H, MeN—), 7.04 (br d, 2H, J=7.69 Hz), 7.29 (br d, 1H, J=7.88 Hz). m/z (%): 377 [M]$^+$ Microanalysis:

|  | C | H | N |
|---|---|---|---|
| Expected: | 63.63% | 7.21% | 3.71% |
| Found: | 63.50% | 7.23% | 3.60% |

EXAMPLE 4
Inhibition of Steroid Sulphatase Activity in MCF-7 cells by oestrone-3-sulphamate Steroid sulphatase is defined as: Steryl Sulphatase EC 3.1.6.2.

Steroid sulphatase activity was measured in vitro using intact MCF-7 human breast cancer cells. This hormone dependent cell line is widely used to study the control of human breast cancer cell growth. It possesses significant steroid sulphatase activity (MacIndoe et al. *Endocrinology*, 123, 1281–1287 (1988); Purohit & Reed, *Int. J. Cancer*, 50, 901–905 (1992)) and is available in the U.S.A. from the American Type Culture Collection (ATCC) and in the U.K. (e.g. from The Imperial Cancer Research Fund). Cells were maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm$^2$ tissue culture flasks were seeded with approximately 1×10$^5$ cells/flask using the above medium. Cells were grown to 80% confluency and medium was changed every third day.

Intact monolayers of MCF-7 cells in triplicate 25 cm$^2$ tissue culture flasks were washed with Earle's Balanced Salt Solution (EBSS from ICN Flow, High Wycombe, U.K.) and incubated for 3–4 hours at 37° C. with 5 pmol (7×10$^5$ dpm) [6,7-$^3$H]oestrone-3-sulphate (specific activity 60 Ci/mmol from New England Nuclear, Boston, Mass., U.S.A.) in serum free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 $\mu$M; 0.1 $\mu$M; 1 $\mu$M). After incubation each flask was cooled and the medium (1 ml) was pipetted into separate tubes containing [$^{14}$C] oestrone (7×10$^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C] oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate. Each batch of experiments included incubations of microsomes prepared from a sulphatase-positive human placenta (positive control) and flasks without cells (to assess apparent non-enzymatic hydrolysis of the substrate). The number of cell nuclei per flask was determined using a Coulter Counter after treating the cell monolayers with Zaponin. One flask in each batch was used to assess cell membrane status and viability using the Trypan Blue exclusion method (Phillips, H. J. (1973) In: *Tissue culture and applications*, [eds: Kruse, D. F. & Patterson, M. K.]; pp. 406–408; Academic Press, New York).

Figure 2:
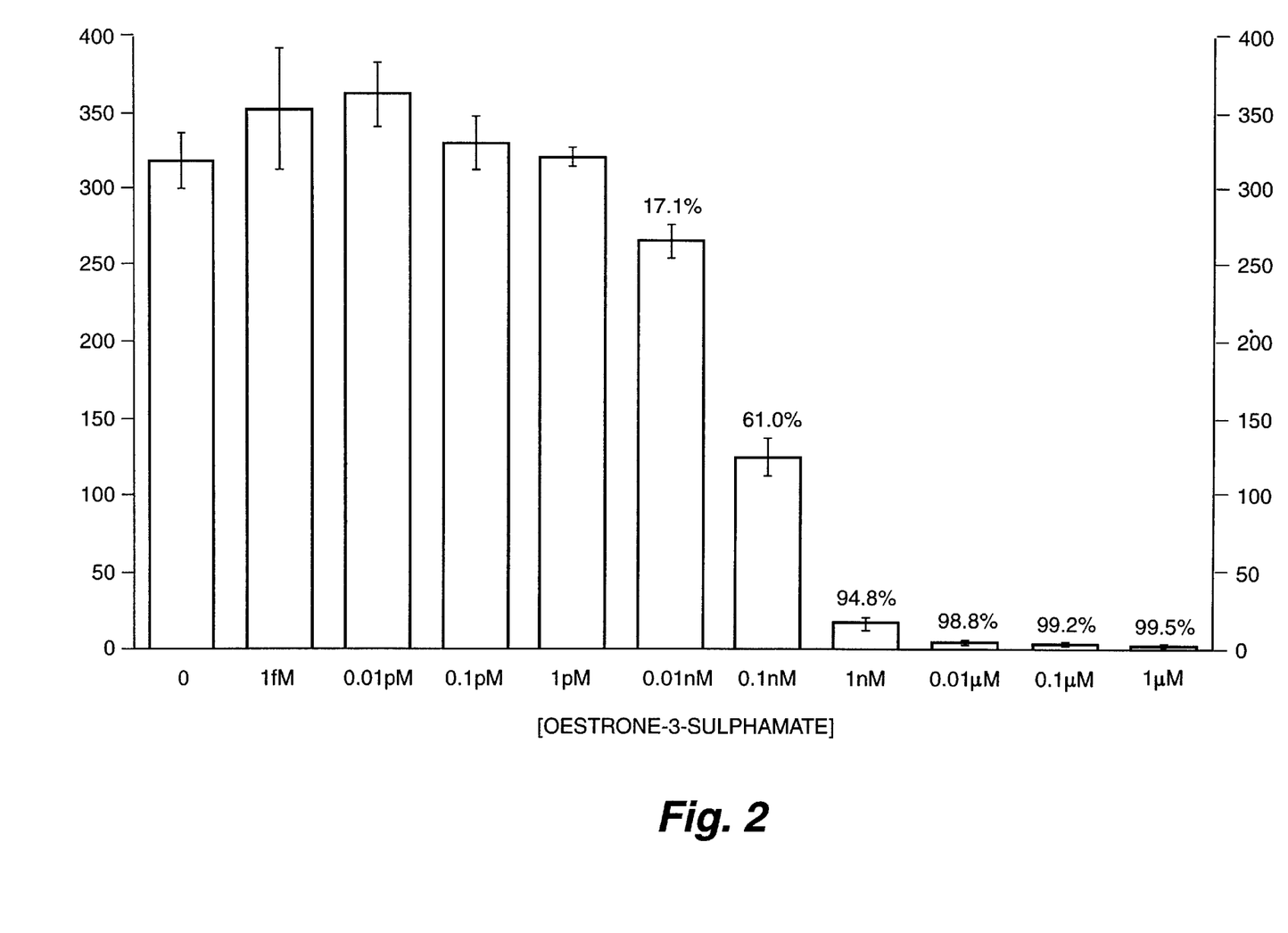
FIG. 2 is a histogram showing the dose-dependent inhibitory effect of oestrone-3-sulphamate on steroid sulphatase activity in human MCF-7 cells in vitro.
Figure 4:
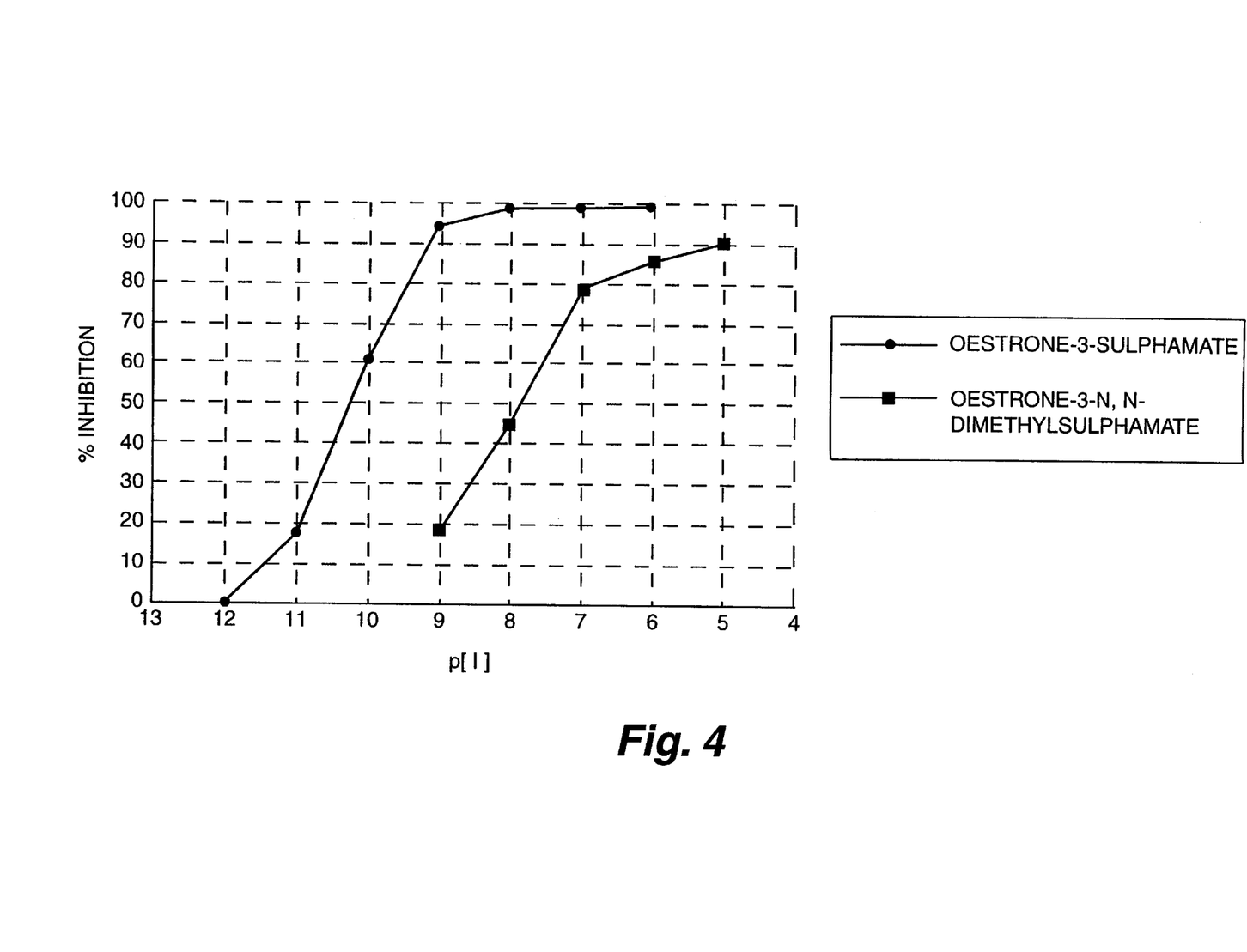
FIG. 4 is a graph comparing the log dose-response curves for oestrone-3-sulphamate and oestrone-3-N,N-dimethylsulphamate on steroid sulphatase activity in human MCF-7 cells in vitro.

Data for oestrone-3-sulphamate are shown in Table I and FIGS. 2 and 4. Results for steroid sulphatase activity are expressed as the mean±1 S.D. of the total product (oestrone+ oestradiol) formed during the incubation period (20 hours) calculated for 10$^6$ cells and, for values showing statistical significance, as a percentage reduction (inhibition) over incubations containing no oestrone-3-sulphamate. Unpaired Student's t-test was used to test the statistical significance of results.

TABLE I

Steroid Sulphatase Activity in, MCF-7 cells in the presence of Oestrone-3-sulphamate

| Oestrone-3-sulphamate concentration | Steroid Sulphatase Activity ¶ (fmol/20 hr/10$^6$ cells) | % reduction over control (% inhibition) |
|---|---|---|
| 0 (control) | 319.7 ± 18.5 | — |
| 1 fM | 353.3 ± 39.0 | — |
| 0.01 pM | 362.3 ± 21.2 | — |
| 0.1 pM | 330.7 ± 17.8 | — |
| 1 pM | 321.8 ± 6.2 | — |
| 0.01 nM | 265.1 ± 11.0* | 17.2% |
| 0.1 nM | 124.8 ± 12.4*** | 60.9% |
| 1 nM | 16.49 ± 4.7*** | 95.0% |
| 0.01 $\mu$M | 3.92 ± 0.4*** | 98.8% |
| 0.1 $\mu$M | 2.53 ± 1.1*** | 99.2% |
| 1 $\mu$M | 1.68 ± 0.7*** | 99.5% |

¶mean ± 1 S.D. n = 3
*p ≤ 0.05
***p ≤ 0.001

EXAMPLE 5
Inhibition of Steroid Sulphatase Activity in MCF-7 cells by oestrone-3-N,N-dimethylsulphamate An identical experimental protocol to that described in Example 4 was used to generate results for oestrone-3-N, N-dimethylsulphamate except that incubations contained oestrone-3-N,N-dimethylsulphamate (5 concentrations: 0; 0.001 $\mu$M; 0.01 $\mu$M; 0.1 $\mu$M; 1 $\mu$M) in place of oestrone-3-sulphamate.

Figure 3:
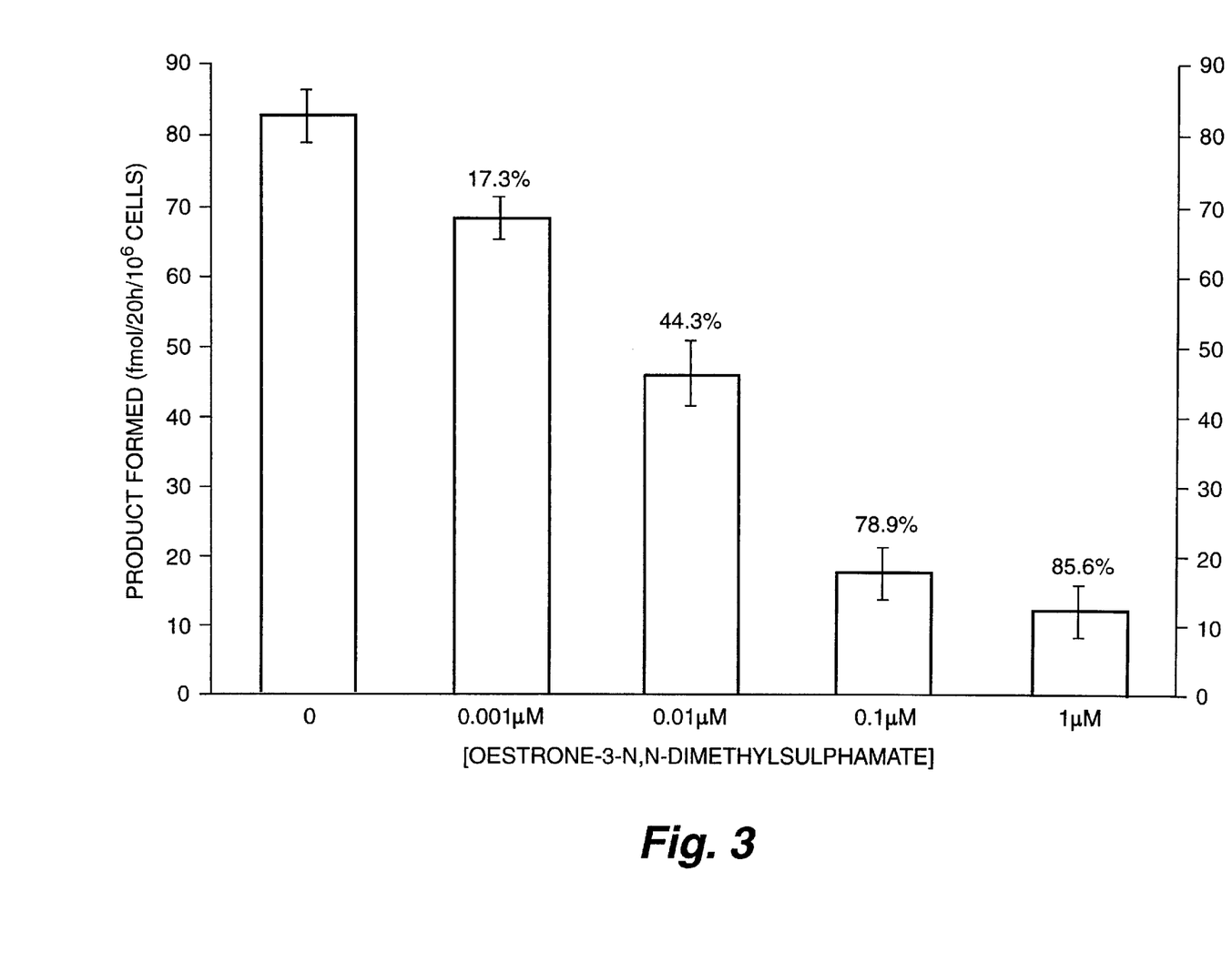
FIG. 3 is a histogram showing the dose-dependent inhibitory effect of oestrone-3-N,N-dimethylsulphamate on steroid sulphatase activity in human MCF-7 cells in vitro.

Results for oestrone-3-N,N-dimethylsulphamate are shown in Table II and FIG. 3 and are expressed in an identical manner to Table I and FIG. 2 respectively. Additionally the log dose-response curve is compared with oestrone-3-sulphamate in FIG. 4.

TABLE 11

Steroid Sulphatase Activity in MCF-7 cells in the presence of oestrone-3-N,N-dimethylsulphamate

| Oestrone-3-N,N-dimethylsulphamate concentration | Steroid Sulphatase Activity ¶ (fmol/20 hr/10$^6$ cells) | % reduction over control (% inhibition) |
|---|---|---|
| 0 (control) | 82.63 ± 3.6 | — |
| 0.001 $\mu$M | 68.33 ± 3.2** | 17.3% |
| 0.01 $\mu$M | 46.0 ± 4.9*** | 44.3% |

TABLE 11-continued

Steroid Sulphatase Activity in MCF-7 cells in the presence of oestrone-3-N,N-dimethylsulphamate

| Oestrone-3-N,N-dimethylsulphamate concentration | Steroid Sulphatase Activity ¶ (fmol/20 hr/$10^6$ cells) | % reduction over control (% inhibition) |
|---|---|---|
| 0.1 µM | 17.43 ± 4.3*** | 78.9% |
| 1 µM | 11.89 ± 37*** | 85.6% |

¶ mean ± 1 S.D. n = 3
**p ≤ 0.01
***p ≤ 0.001

EXAMPLE 6
Inhibition of Steroid Sulphatase Activity in MCF-7 cells by pre-treatment with oestrone-3-N,N-dimethylsulphamate and oestrone-3-N,N-dimethylsulphamate A similar experimental protocol to that described in Example 4 was used to determine the effect of pre-treating MCF-7 cells with oestrone-3-sulphamate and oestrone-3-N, N-dimethylsulphamate respectively.

Intact monolayers were initially incubated for 2 hours at 37° C. with 0.1 µM oestrone-3-sulphamate, oestrone-3-N, N-dimethylsulphamate or medium alone (control). The medium bathing the cells was then removed by aspiration and cells were washed 3 times successively with 5 ml of medium on each occasion. The resultant 'washed' cells were then re-suspended and incubated for 3–4 hours at 37° C. in medium containing 5 pmol (7×$10^5$ dpm) [6,7-$^3$H]oestrone-3-sulphate. All other aspects were identical to those described in Examples 3 and 4.

Results for oestrone-3-sulphamate and oestrone-3-N,N-dimethylsulphamate are shown in Table III and are expressed in a similar manner to Table I.

TABLE III

Steroid Sulphatase Activity in MCF-7 cells pre-incubated with oestrone-3-sulphamates

| Pre-treatment | Steroid Sulphatase Activity ¶ (fmol/20 hr/$10^6$ cells) | % reduction over control (% inhibition) |
|---|---|---|
| Control | 65.4 ± 6.4 | — |
| Oestrone-3-sulphamate | 1.7 ± 0.2*** | 97.4% |
| Oestrone-3-N,N-dimethylsulphamate | 53.1 ± 3.4* | 18.8% |

¶ mean ± 1 S.D. n = 3
*p ≤ 0.05
*p ≤ 0.001

EXAMPLE 7
Inhibition of Steroid Sulphatase Activity in Placental Microsomes by Oestrone-3-sulphamate Sulphatase-positive human placenta from normal term pregnancies (Obstetric Ward, St. Mary's Hospital, London) were thoroughly minced with scissors and washed once with cold phosphate buffer (pH 7.4, 50 mM) then re-suspended in cold phosphate buffer (5 ml/g tissue). Homogenisation was accomplished with an Ultra-Turrax homogeniser, using three 10 second bursts separated by 2 minute cooling periods in ice. Nuclei and cell debris were removed by centrifuging (4° C.) at 2000 g for 30 minutes and portions (2 ml) of the supernatant were stored at –20° C. The protein concentration of the supernatants was determined by the method of Bradford (*Anal. Biochem.*, 72, 248–254 (1976)).

Incubations (1 ml) were carried out using a protein concentration of 100 µg/ml, substrate concentration of 20 µM [6,7-$^3$H]oestrone-3-sulphate (specific activity 60 Ci/mmol from New England Nuclear, Boston, Mass., U.S.A.) and an incubation time of 20 minutes at 37° C. Eight concentrations of oestrone-3-sulphamate were employed: 0 (i.e. control); 0.05 µM; 0.1 µM; 0.2 µM; 0.4 µM; 0.6 µM; 0.8 µM; 1.0 µM. After incubation each sample was cooled and the medium (1 ml) was pipetted into separate tubes containing [$^{14}$C]oestrone (7×$10^3$ dpm) (specific activity 97 Ci/mmol from Amersham International Radiochemical Centre, Amersham, U.K.). The mixture was shaken thoroughly for 30 seconds with toluene (5 ml). Experiments showed that >90% [$^{14}$C]oestrone and <0.1% [$^3$H]oestrone-3-sulphate was removed from the aqueous phase by this treatment. A portion (2 ml) of the organic phase was removed, evaporated and the $^3$H and $^{14}$C content of the residue determined by scintillation spectrometry. The mass of oestrone-3-sulphate hydrolysed was calculated from the $^3$H counts obtained (corrected for the volumes of the medium and organic phase used, and for recovery of [$^{14}$C]oestrone added) and the specific activity of the substrate.

Figure 5:
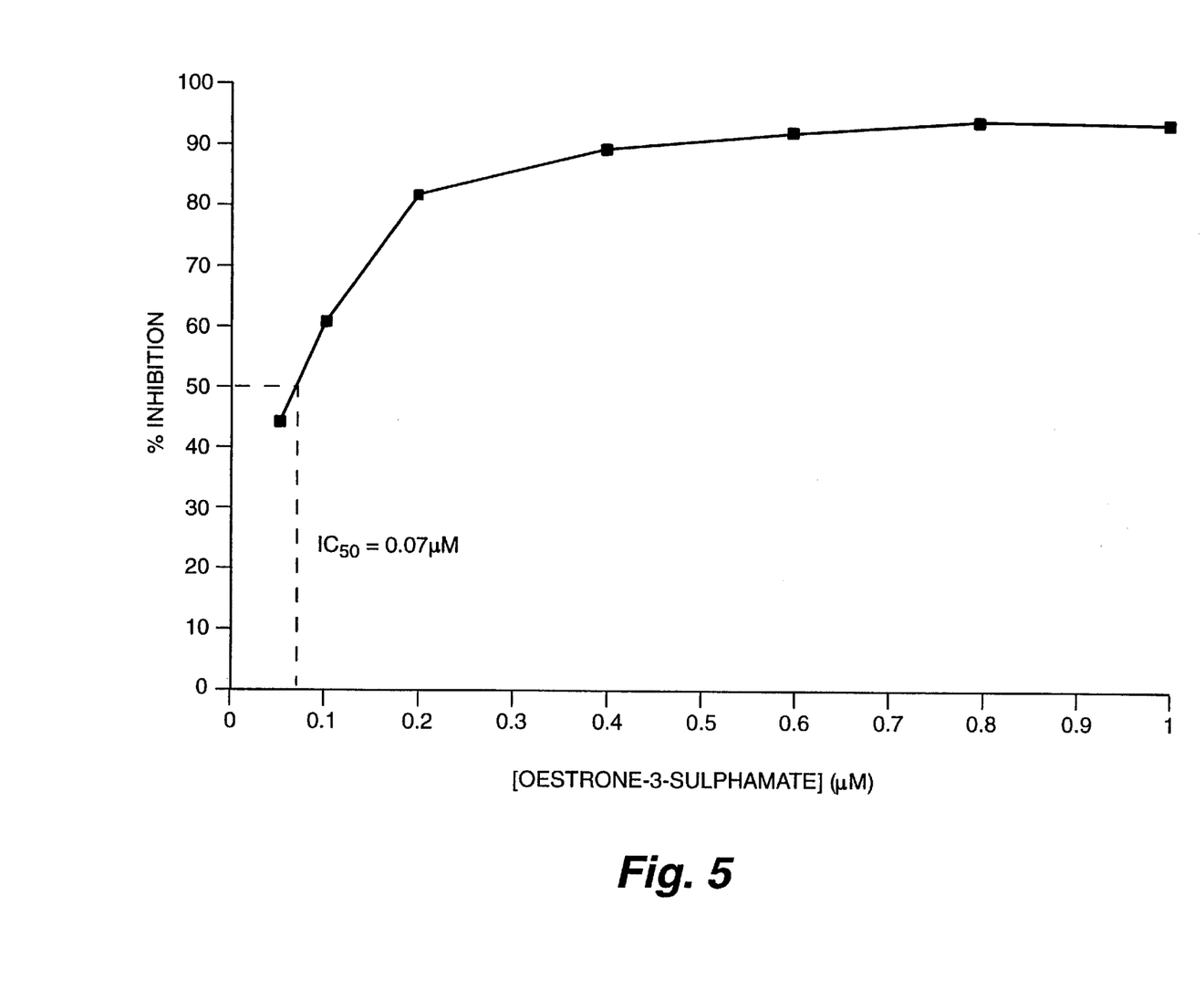
FIG. 5 is a graph showing the dose-dependent inhibitory effect of oestrone-3-sulphamate, together with its $IC_{50}$ value (concentration required to produce 50% inhibition), on steroid sulphatase activity in human placental microsomes in vitro.

Results for oestrone-3-sulphamate are shown in Table IV and FIG. 5. Results for steroid sulphatase activity are expressed in Table IV as total product (oestrone+oestradiol) formed during the incubation period (time) and as a percentage reduction (inhibition) over incubations containing no oestrone-3-sulphamate which acted as control. Results for steroid sulphatase activity are expressed in FIG. 4 as percentage reduction (inhibition) over control against concentration of oestrone-3-sulphamate and include the calculated $IC_{50}$ value (i.e. the concentration of oestrone-3-sulphamate which produces 50% inhibition in relation to control) of 0.07 µM.

TABLE IV

Steroid Sulphatase Activity in placental microsomes in the presence of Oestrone-3-sulphamate

| Oestrone-3-sulphamate concentration | Steroid Sulphatase Activity ¶ (pmol/hr/ 0.1 mg protein) | % reduction over control (% inhibition) |
|---|---|---|
| 0 (control) | 768.6 | — |
| 0.05 µM | 430.4 | 44.0% |
| 0.1 µM | 305.9 | 60.2% |
| 0.2 µM | 140.0 | 81.8% |
| 0.4 µM | 83.3 | 89.2% |
| 0.6 µN | 61.8 | 92.0% |
| 0.8 µM | 49.2 | 93.6% |
| 1.0 µM | 51.6 | 93.3% |

¶ mean of 2 estimates

EXAMPLE 8
Inhibition of Steroid Sulphatase Activity in Liver Microsome Preparations from Rats treated with subcutaneous Oestrone-3-sulphamate Four groups of 3 female Wistar rats (weight range 80–110 g) were given 100 µl subcutaneous injections (once daily for 7 days, vehicle: propylene glycol) of either:

Propylene glycol (vehicle control)
Oestrone-3-sulphamate (10 mg/kg/day)
Oestrone-3-sulphate (10 mg/kg/day) (substrate control)
Oestrone-3-sulphate (10 mg/kg/day)+Oestrone-3-sulphamate (10 mg/kg/day)

On the eighth day all rats were sacrificed and livers were removed by dissection. Liver microsomal preparations were prepared by an identical protocol to that described in Example 6 except that the tissue source was rat liver and that duplicate experiments to determine steroid sulphatase activity were performed using [6,7-$^3$H]oestrone-3-sulphate and [7-$^3$H]dehydroepiandrosterone-3-sulphate as separate substrates.

Results for steroid sulphatase activity are shown in Table V and are expressed as total product formed during the incubation period in the form of mean±1 S.D. Results for incubations of tissue obtained from groups of rats treated with oestrone-3-sulphamate are also expressed as a percentage reduction (inhibition) in steroid sulphatase activity compared to their respective controls.

TABLE V

Steroid Sulphate Activity in Liver Microsome Preparations from Rats treated with subcutaneous Oestrone-3-sulphamate

| Treatment Group | Assay Substrate | Steroid Sulphatase Activity ¶ (nmol/30 min/200 µg protein) | % reduction over control |
|---|---|---|---|
| control (vehicle) | E$_1$-S | 20.95 ± 0.2 | — |
| E$_1$-SO$_3$NH$_2$ | E$_1$-S | 0.34 ± 0.1*** | 98.4% |
| control (E$_1$-S) | E$_1$-S | 20.6 ± 0.4 | — |
| E$_1$-S + E$_1$-SO$_3$NH$_2$ | E$_1$-S | 0.21 ± 0.03*** | 99.0% |
| control (vehicle) | DHA-S | 1.73 ± 0.4 | — |
| E$_1$-SO$_3$NH$_2$ | DHA-S | 0.1 ± 0.01*** | 94.2% |
| control (E1-S) | DHA-S | 1.71 ± 0.1 | — |
| E$_1$-S + E$_1$-SO$_3$NH$_2$ | DHA-S | 0.09 ± 0.01*** | 94.7% |

¶ mean ± 1 S.D. n = 3
***P ≦ 0.001
E$_1$-S = oestrone-3-sulphamate
DHA-S = dehydroepiandrosterone-3-sulphate
E$_1$-SO$_3$NH$_2$ = oestrone-3-N,N-dimethylsulphamate

We claim:

1. A method of inhibiting steroid sulphatase activity in a patient in need of same, the method comprising administering to said patient a steroid sulphatase inhibiting amount of a ring system compound which comprises a polycyclic ring to which is attached a sulphamate group of the formula wherein each of R$_1$ and R$_2$ is independently selected from H, alkyl, alkenyl, cycloalkyl and aryl, or together represent alkylene optionally containing one or more hetero atoms or groups in the alkylene chain; and wherein said compound is an inhibitor of an enzyme having steroid sulphatase activity (EC 3.1.6.2); and when the sulphamate group of said compound is replaced with a sulphate group to form a sulphate compound and incubated with a steroid sulphatase enzyme (EC 3.1.6.2) at a pH 7.4 and 37° C. it provides a K$_m$ value of less than 50 µM.

2. A method according to claim 1 wherein the ring system compound comprises a six membered ring to which is attached the sulphamate group.

3. A method according to claim 2, wherein the six membered ring is a six membered carbon ring to which is attached the sulphamate group.

4. A method according to claim 1 wherein at least one of R$_1$ and R$_2$ is hydrogen.

5. A method according to claim 1 wherein the ring is a sterol.

6. A method according to claim 5, wherein the sterol is a 3-sterol.

7. A method according to claim 6, wherein the sterol is selected from the group consisting of oestrone, dehydroepiandrosterone, substituted oestrone, substituted dehydroepiandrosterone, oestradiol, substituted oestradiol, oestriol and substituted oestriol.

8. A method according to claim 1, wherein at least one of R$_1$ and R$_2$ substituent is C$_1$–C$_{10}$ alkyl.

9. A method according to claim 8, wherein at least one of R$_1$ and R$_2$ is C$_1$–C$_5$ alkyl.

* * * * *